US012750619B2

(12) United States Patent
Polinger

(10) Patent No.: US 12,750,619 B2
(45) Date of Patent: Sep. 29, 2026

(54) CUSTOMIZED AUDIO MODIFICATION TOOL

(71) Applicant: Microsoft Technology Licensing, LLC, Redmond, WA (US)

(72) Inventor: Anton V. Polinger, Bellevue, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 152 days.

(21) Appl. No.: 18/756,883

(22) Filed: Jun. 27, 2024

(65) Prior Publication Data

US 2026/0006378 A1 Jan. 1, 2026

(51) Int. Cl.

| | |
|---|---|
| ***H04R 3/04*** | (2006.01) |
| ***A61B 5/12*** | (2006.01) |
| ***G06F 3/16*** | (2006.01) |

(52) U.S. Cl.

CPC ............... *H04R 3/04* (2013.01); *A61B 5/123* (2013.01); *G06F 3/162* (2013.01); *H04R 2430/01* (2013.01)

(58) Field of Classification Search

CPC ............ H04R 3/04; A61B 5/123; G06F 3/162

See application file for complete search history.

(56) References Cited

U.S. PATENT DOCUMENTS

| | | | | |
|---|---|---|---|---|
| 11,902,747 | B1 * | 2/2024 | Morris | H04R 25/507 |
| 2014/0309549 | A1 * | 10/2014 | Selig | A61B 5/123 600/559 |
| 2019/0109804 | A1 * | 4/2019 | Fu | A63F 13/215 |
| 2024/0024781 | A1 * | 1/2024 | Mccoy | G10H 1/0025 |

OTHER PUBLICATIONS

"Jabra Sound+ App", Retrieved from: https://www.jabra.com/en-in/software-and-services/apps/jabra-sound-plus, Retrieved on: Jun. 25, 2025, 5 pages.

* cited by examiner

*Primary Examiner* — Olisa Anwah

(57) ABSTRACT

A method and system for providing a customized configuration of settings for an audio processor. The customized configuration is determined for a user based on results of a hearing test. The test may be provided by the system or another system. The customized configuration includes an increase or decrease to an intensity level of one or more frequency bands of one or more channels (e.g., a left and right) to compensate for a decreased hearing threshold level experienced by the user (e.g., as indicated by the hearing test results). The settings may be further adjusted based on an application of one or more equal-loudness contours representing varying sensitivity of the human ear to different frequencies. When audio is played by an application including or in communication with the audio processor, the audio is adjusted based on the customized configuration and the user is provided with an improved listening experience.

20 Claims, 11 Drawing Sheets

CUSTOMIZED AUDIO MODIFICATION TOOL

BACKGROUND

Due to age, encountering various environmental factors, genetic factors, and/or other circumstances, a person can experience and be afflicted by partial hearing loss. When experiencing hearing loss, the person's ability to hear different frequencies varies. For instance, some frequencies are more easily detected by than other frequencies. As a result of hearing loss, audio can be perceived as muffled, where speech, music, and/or ambient sounds lose clarity and/or distinctiveness. Additionally, perception of spatial characteristics may become distorted, where the ability to perceive the depth, distance, and/or direction of sounds in the environment may be impaired.

It is with respect to these and other considerations that examples have been made. In addition, although relatively specific problems have been discussed, it should be understood that the examples should not be limited to solving the specific problems identified in the background.

SUMMARY

The technology described herein provides a customized configuration of settings to modify audio based on results of a hearing test. A method and system are described that determine a customized configuration of settings to process audio content and create audio output that optimizes clarity of the audio content for a user. The test may be provided by the system or by another system. In some examples, determining the customized configuration comprises determining increases and/or decreases to an intensity level of one or more frequency bands of one or more channels (e.g., a left and right) that compensate for a decreased hearing threshold level experienced by the user (e.g., as indicated by the hearing test results). In further examples, determining the customized configuration comprises determining a maximum and minimum intensity threshold for applying dynamic range compression to amplify softer sounds that are below the minimum intensity threshold and limit amplification of louder sounds that are above the maximum intensity threshold. In yet further examples, determining the customized configuration comprises determining dynamic gain control settings by applying dynamic range enhancement to improve perceived signal-to-noise ratios. In further examples, determining the customized configuration comprises determining a range of frequency bands to shift/transpose affected frequency bands to where the user's hearing sensitivity is better, allowing them to perceive audio in those frequencies more easily. In some examples, determining the customized configuration further comprises applying one or more equal-loudness contours representing varying sensitivity of the human ear to different frequencies to further adjust the intensity level of one or more frequency bands of one or more channels. In yet further examples, one or more audio filters and/or other audio modification techniques are applied to address hearing needs of the user. When audio is played by an application including or in communication with the equalizer, the audio is adjusted based on the customized configuration and the user is provided with an improved listening experience. Some types of audio content may require permission prior to adjusting the audio or may prohibit one or more types of audio adjustments.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

The present disclosure is illustrated by way of example by the accompanying figures, in which like references indicate similar elements. Elements in the figures are illustrated for simplicity and clarity and have not necessarily been drawn to scale.

DETAILED DESCRIPTION

Aspects described herein provide a customized configuration of settings of an audio processor. The audio processor adjusts audio content via one or more techniques, such as frequency equalization (e.g., boosting or attenuating intensity/volume levels of different frequency bands in an audio signal), dynamic range compression (e.g., compressing the dynamic range of the audio content), dynamic range enhancement (e.g., improving the perceived signal-to-noise ratios), and/or frequency transposition (e.g., transposing audio from one frequency range to another using linear frequency scaling, logarithmic frequency scaling, non-linear frequency compression, or other processing techniques) based on the customized configuration of settings.

The customized configuration is determined for a user based on results of a hearing test performed on the user. The adjustments to audio content compensate for a decreased hearing threshold level experienced by the user at one or more frequency bands (e.g., as indicated by the hearing test results). In some examples, one or more equal-loudness contours are applied to further adjust intensity levels to compensate for varying sensitivity of the human ear to different frequencies. When audio is played by an application including or in communication with the audio processor, the audio is adjusted based on the customized configuration and the user is provided with an improved listening experience, where clarity and intelligibility of the audio is increased for the user.

In some implementations, to compensate for a user's distorted perception of spatial characteristics of audio (e.g., as detected in the hearing test), the audio processor may further employ spatial and/or multi-channel audio techniques and/or make adjustments to associated settings. In examples, the spatial and/or multi-channel audio techniques and/or associated settings adjustments may enhance the user's perception of characteristics, such as the directionality and distance of sounds. Example spatial and/or multi-channel audio techniques may include binaural rendering (e.g., simulating the way sound naturally reaches the user's two ears to create a sense of three-dimensional space), head-related transfer function (HRTF) adjustments (e.g., personalizing spatial audio based on the unique shape of a user's ears and head as detected by the hearing test), and/or ambisonics (e.g., encoding full-sphere surround sound).

Figure 1A:
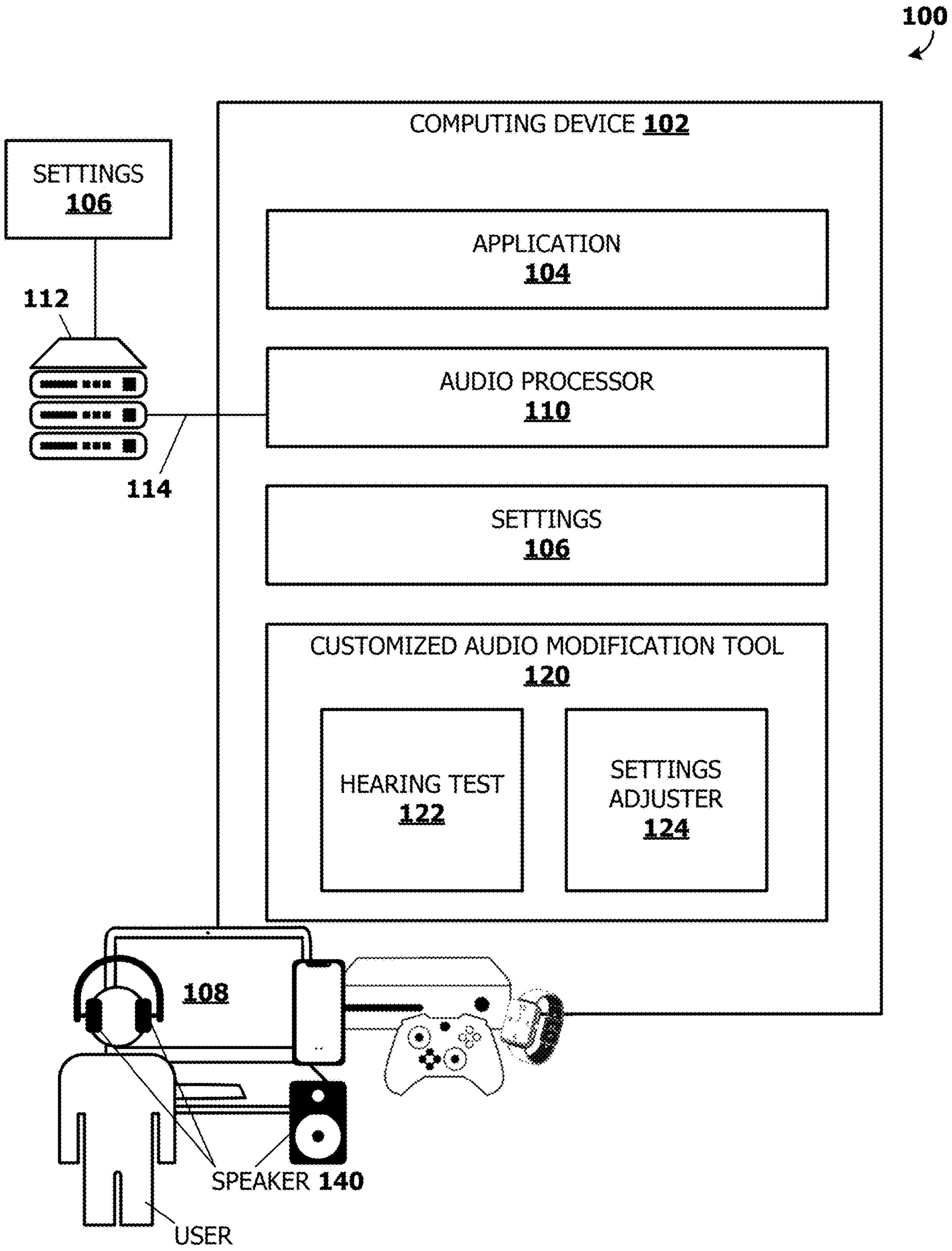
FIG. 1A is a diagram of an example system in which an customized audio modification tool may be implemented according to an aspect.
Figure 6:
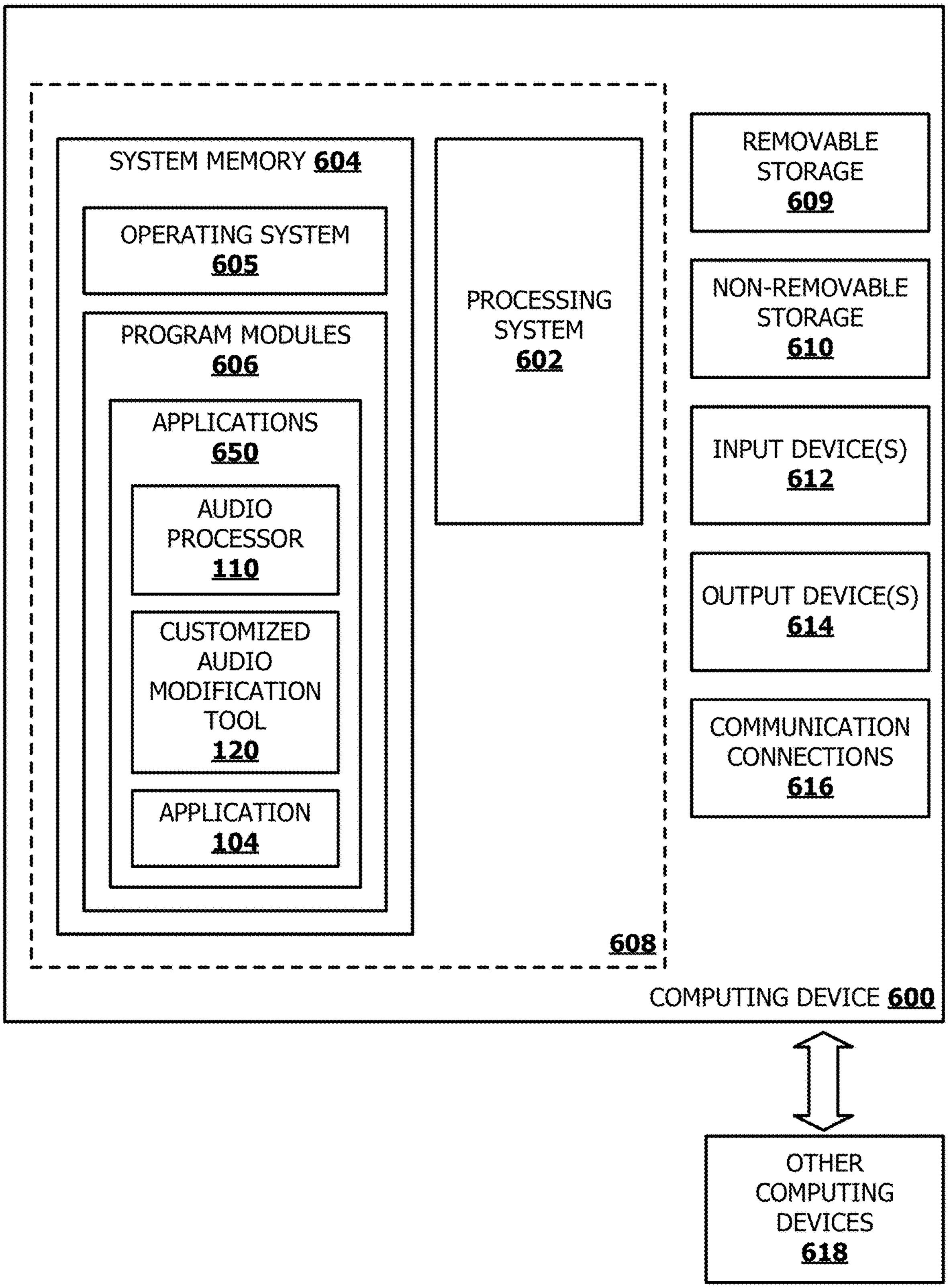
FIG. 6 is a block diagram illustrating example physical components of a computing device with which aspects of the disclosure may be practiced.

With reference now to FIG. 1A, a diagram of an example system 100 is depicted in which a customized audio modification tool 120 may be implemented in accordance with examples described herein. The example system 100, as depicted, is a combination of interdependent components that interact to form an integrated whole. Some components are illustrative of software applications, systems, or modules that operate on a computing device or across a plurality of computer devices. Any suitable computer device(s) may be used, including web servers, application servers, network appliances, dedicated computer hardware devices, virtual server devices, personal computers, a system-on-a-chip (SOC), or any combination of these and/or other computing devices known in the art. In one example, components of systems disclosed herein are implemented on a single processing system. The processing system provides an operating environment for software components to execute and utilize resources or facilities of such a system. Examples of a processing system comprising such an operating environment are depicted in FIG. 6. In another example, the components of systems disclosed herein are distributed across multiple processing systems. For instance, input may be entered on a user device or client device and information may be processed on or accessed from other devices in the network, such as one or more remote cloud devices or web server devices. The network may include one or more local area networks (LANs) and/or wide area networks (WANs). In example implementations, a network includes the Internet, an intranet, and/or a cellular network, amongst any of a variety of possible public and/or private networks.

Among other components not shown, the system 100 includes a computing device 102. The computing device 102 can take a variety of forms, including, for example, a desktop computer, laptop, tablet, smart phone, wearable device, gaming device/platform, virtualized reality device/platform (e.g., virtual reality (VR), augmented reality (AR), mixed reality (MR)), etc. In examples, a user of the computing device 102 is a user of a plurality of various types of computing devices 102. In some examples, the computing device 102 has an operating system that provides a graphical user interface (GUI) that allows users to interact with the computing device 102 via graphical elements, such as application windows (e.g., display areas), buttons, icons, and the like. For example, the graphical elements are displayed on a display screen 108 of the computing device 102 and can be selected and manipulated via user inputs received via a variety of input device types (e.g., keyboard, mouse, stylus, touch, spoken commands, gestures).

In examples, the computing device 102 includes applications 104 for performing different tasks, such as media playback, gaming, communicating, web browsing, data processing, information gathering and/or management, data manipulation, virtualized assisting, narration, visual construction, resource coordination, software development, calculations, etc. In some examples, one or more applications 104 are hosted on a remote server 112 accessed by the computing device 102 over a network connection 114. According to an aspect, at least one application 104 includes functionality to play sound (e.g., audio output) via the computing device 102. As an example, the application 104 is or includes a media player that reads audio content in one or various formats (e.g., MPEG-1 Audio Layer III or MPEG-2 Audio Layer III (MP3), Waveform Audio File Format (WAV), Free Lossless Audio Codec (FLAC), Advanced Audio Coding (AAC), Ogg Vorbis, Windows Media Audio (WMA), Audio Interchange File Format (AIFF), and/or other audio formats). The application 104 decodes audio content, if necessary (e.g., for compressed formats), and plays the audio content for the user. In some examples, the application 104 handles one or more of various types of streaming methods, such as Hypertext Transfer Protocol (HTTP) Live Streaming (HLS), Dynamic Adaptive Streaming over HTTP (DASH), Real-Time Messaging Protocol (RTMP), etc. As another example, the application 104 is a phone application that receives audio content of a phone call in one or various formats (e.g. Adaptive Multi-Rate (AMR) or other codecs). The application 104 further sends the audio content to a sound card included in (or in communication with) the computing device 102 to be played on one or more speakers 140.

The speaker(s) 140 are included in and/or connected to the computing device 102 and generate audio output (e.g., audible sound that is output into an environment). For instance, the audio output includes sound waves created by the speaker(s) 140 based on signals received from the sound card, where the sound waves have specific frequencies controlling pitch of the sound (e.g., how high or low the frequency of the sound is) and amplitudes controlling volume of the sound (e.g., how loud or quiet the sound is). In examples, a user of the computing device 102 is located in the environment, where the audio output provided by the speaker(s) 140 is detected and interpreted by the user. The speaker(s) 140 may include an internal speaker (e.g., internal to the computing device 102) and/or an external speaker connected to the computing device 102 by a wire or wirelessly connected to the computing device 102. In some examples, the external speaker(s) 140 are incorporated into a unit or set worn by the user, such as a headset, earphones, earbuds, a helmet, etc.

In some examples, the computing device 102 includes an audio processor 110. The audio processor 110 is a device or a software application used to adjust characteristics of an audio signal based on configurable settings 106. In other examples, the audio processor 110 operates on a remote server 112 and communicates with one or a plurality of the user's computing devices 102 over one or more network connections 114. In further examples, the configurable settings 106 are stored on the server 112 and are accessible by the audio processor 110. In some examples, the audio processor 110 uses equalization techniques to boost or attenuate volume levels of different frequency bands (e.g., bass, midrange, treble) in audio. In other examples, the audio processor 110 uses dynamic range compression techniques to compress the range of volume levels present in an audio signal. For instance, dynamic range compression techniques may be used to reduce the volume of louder sounds and/or amplify softer sounds. Compressing the dynamic range of audio content can help to prevent distortion caused by audio signals that are above an intensity threshold and can also make quiet sounds (e.g., below an intensity threshold) more audible. In further examples, the audio processor 110 uses frequency transposition techniques to shift particular frequencies to another frequency range (e.g., using linear frequency scaling, logarithmic frequency scaling, non-linear frequency compression, and/or other processing techniques). In yet further examples, the audio processor 110 uses dynamic range enhancement techniques (e.g., audio multiband compression) to dynamically modify an audio signal's gain. Dynamic range enhancement may be applied to individually frequency bands. For example, if a specific frequency band has a low perceived signal-to-noise ratio, the dynamic range enhancement can amplify the gain for that frequency band, thereby strengthening the signal. Alternatively, dynamic range enhancement can set a limit on a frequency band to prevent stronger signals from causing distortion to audio output. In other examples, the audio processor 110 uses spatial or multi-channel audio techniques to enhance the user's perception of the directionality and distance of sounds. For instance, the audio processor 110 may use binaural rendering techniques to simulate the way sound naturally reaches the user's two ears. As another example, the audio processor 110 may use HRTF adjustments to personalize spatial audio (e.g., based on the unique shape of the user's ears and head). In the case of multi-channel audio, the audio processor 110 may alter the distribution of sound across multiple speakers 140 to adjust spatial perception. Furthermore, the audio processor 110 may employ ambisonics, a full-sphere surround sound technique that encodes the directionality and distance of sounds. Additional and/or alternative spatial and multi-channel audio techniques may be used to improve the user's perception of audio content, compensating for any distorted perception of spatial characteristics that the user may experience.

Figure 1B:
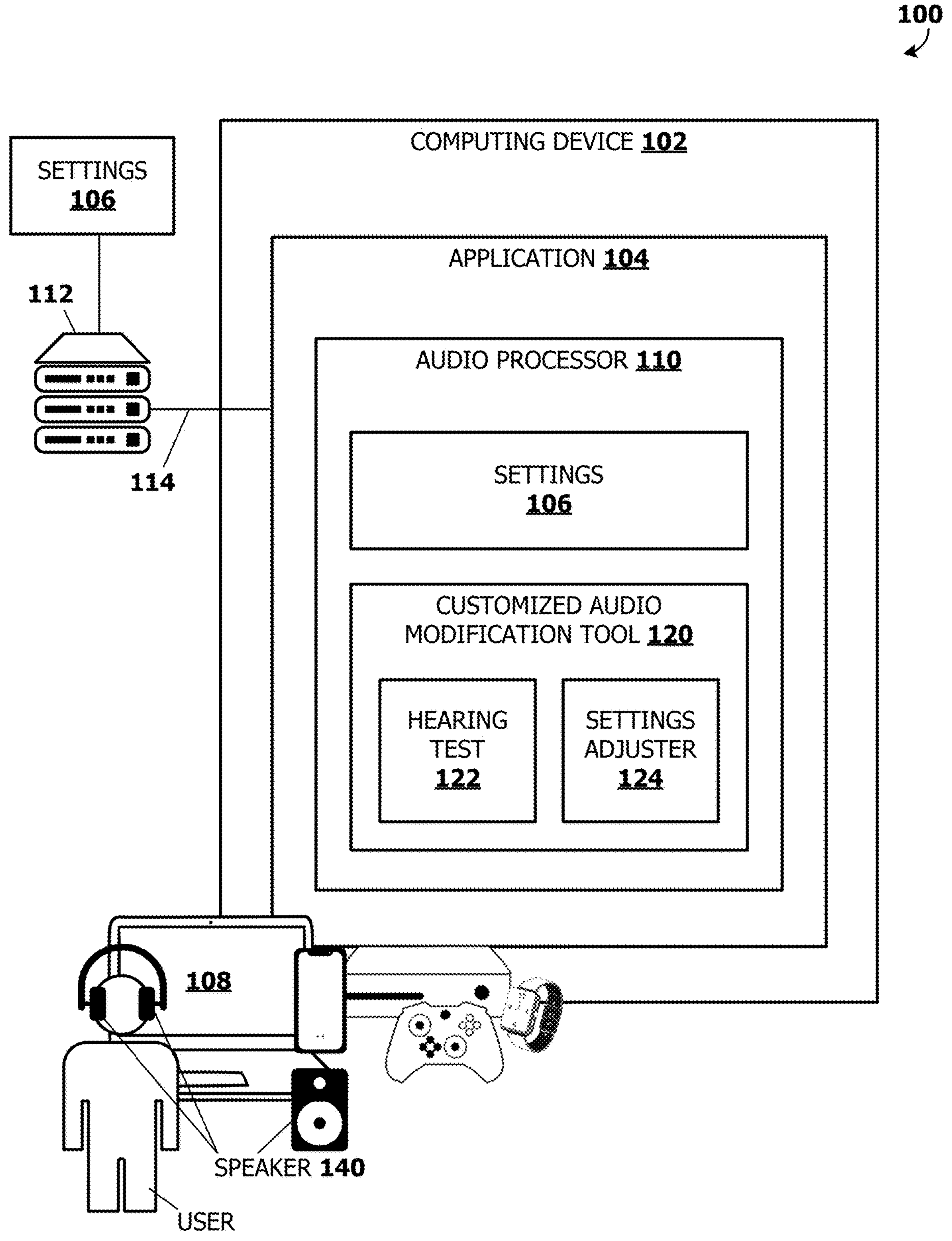
FIG. 1B is a diagram of another example system in which the customized audio modification tool may be implemented according to an aspect.

In some implementations (and as depicted in FIG. 1A), the audio processor 110 is an independent application or is included in the sound card and one or more applications 104 are in communication with the audio processor 110 to adjust the sound profile of audio output played by the application(s) 104. In other implementations (and as depicted in FIG. 1B), the audio processor 110 is included in an application 104 and adjusts the sound profile of audio output played by that application 104. In examples, the audio processor 110 provides a user interface (UI) that allows interaction with one or more configurable parameters (settings 106) to adjust audio output according to their preferences or needs. Example settings adjustments include alterations in gain or amplitude of specific frequency bands (e.g., increasing or decreasing the loudness/intensity of specific frequencies), manipulation of center frequencies, control over quality-(Q-) factors or bandwidths, frequency transposition, utilization of predefined presets tailored for distinct audio playback environments or music genres, and/or additional adjustments. The Q-factor is a dimensionless parameter that describes how underdamped an oscillator or resonator is.

In some examples, the UI is graphical and includes sliders or knobs representing different frequency bands and other adjustable settings 106 with which the user interacts. In other examples, the UI is textual or numerical. In examples, adjustments made to the settings 106 causes an adjustment to the audio output's frequency response (e.g., volume level of one or more frequency bands) according to the settings 106. Oftentimes, adjusting settings 106 is beyond the scope of knowledge for an average user. For instance, while the sliders, knobs, or other UI elements may be easily manipulated by the user, the user may not have the expertise to know what adjustments the manipulations are causing to audio output. Further, the user likely does not have the expertise to know what configuration of settings 106 produce audio output that is improved for the user (e.g., compensates for hearing loss experienced by the user).

According to aspects, the system 100 includes a customized audio modification tool 120 that determines a customized configuration of settings 106 for the user and applies the configuration to the audio processor 110. For instance, the customized configuration compensates for hearing loss experienced by the user and allows for audio output played by the application 104 to be better heard by the user by altering gain or amplitude, manipulating center frequencies, and/or controlling Q-factors or bandwidths of one or more frequency bands, utilizing a predefined preset, and/or additional or alternative equalizer setting adjustments. In some implementations, the customized audio modification tool 120 is a functionality provided by the audio processor 110 (e.g., as depicted in FIG. 1B). In other implementations (and as depicted in FIG. 1A), the customized audio modification tool 120 is a separate application in communication with and used by the audio processor 110. In some implementations, the customized audio modification tool 120 is located locally on the computing device 102. In other implementations, the customized audio modification tool 120 is remotely located on the server 112.

According to examples, the customized audio modification tool 120 determines the customized configuration of settings 106 based on results of a hearing test 122. In some implementations, the hearing test 122 is provided to the user by the customized audio modification tool 120. In other implementations, the hearing test 122 is provided by another application 104 or device and the results of the hearing test 122 are received by the customized audio modification tool 120. The hearing test 122 may be one of various types of hearing tests. In some examples, the hearing test 122 is a tone audiometry test that measures the softest sound the user can detect at different frequencies. For instance, in the hearing test 122, test sounds are played at various frequencies and intensity levels to the user via one or more speakers 140, user responses (e.g., user input via a user input device) to the test sounds are received, and the user's hearing thresholds based on the user responses to the various test sounds are determined. In some examples, the results of the hearing test 122 include a measurement of the user's ability to hear sounds based on frequency and intensity.

In some implementations, the hearing test 122 includes a spatial audio perception test that assesses the user's ability to perceive the direction and distance of sounds. In some examples, sounds are played from various directions and distances relative to the user using multiple speakers 140 (e.g., a surround sound method). This surround sound method tests the user's ability to perceive and locate sounds in a three-dimensional space. In other examples, sounds are played by one speaker 140 or by multiple speakers 140 that have spatial audio capabilities to simulate an experience of sounds coming from different directions and distances to test the user's spatial hearing capabilities.

In further examples, the user's ability to hear the test sounds, and thus the test results, are influenced by the speaker(s) 140 (e.g., the speaker 140 or one of multiple speakers produces distorted audio output at a particular frequency band). In yet further examples, the user's ability to hear the test sounds and the test results are additionally influenced by the environment (e.g., background noise and the absorption and/or reflection of different frequencies by the environment).

Figure 2:
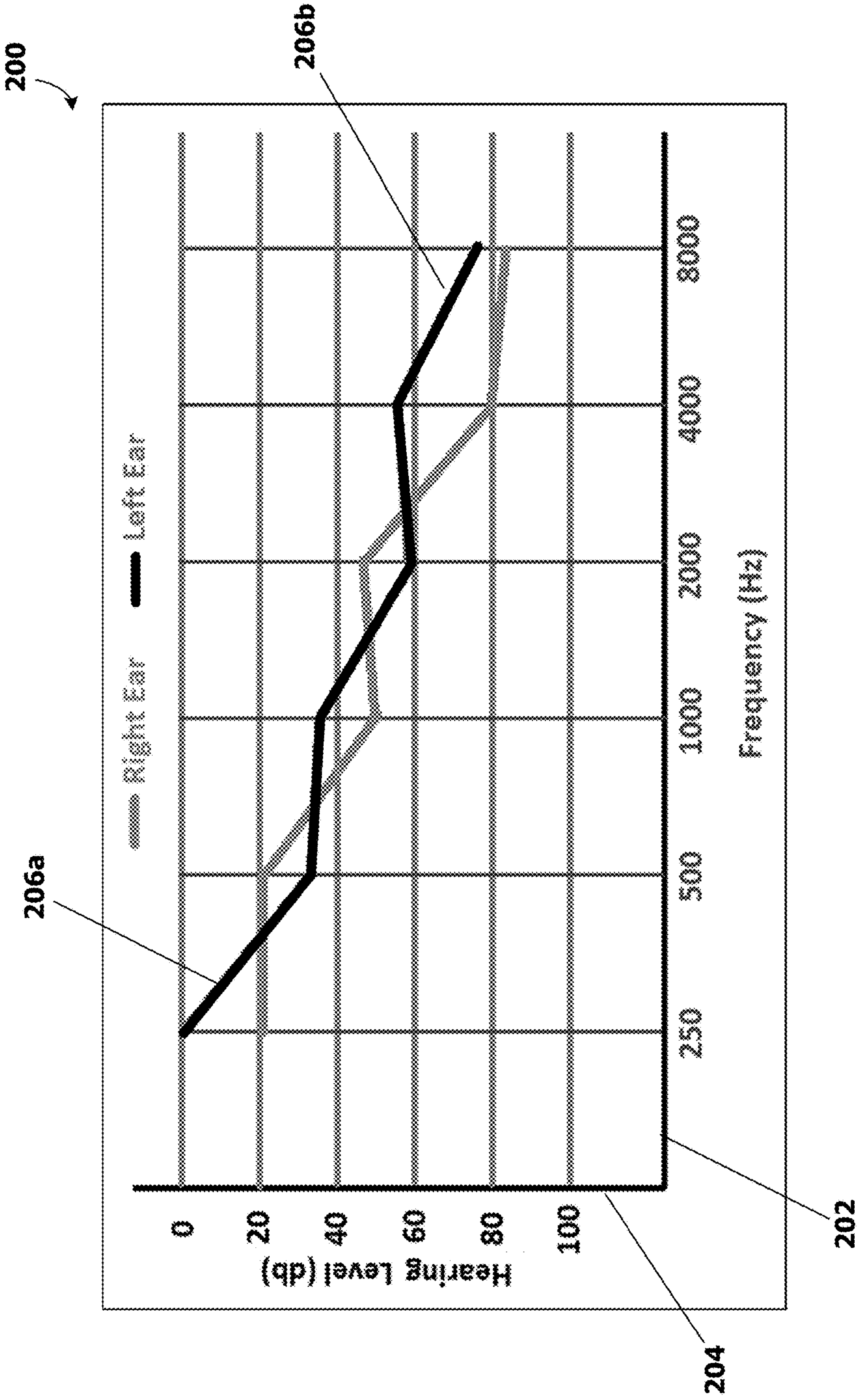
FIG. 2 depicts example hearing test results according to an aspect.

Example test results 200 are depicted in FIG. 2. In FIG. 2, the example test results 200 are represented in an audiogram with a first axis 202 (e.g., X-axis) representing frequency (e.g., measured in Hertz (Hz)) and a second axis 204 (e.g., Y-axis) representing the user's hearing level (e.g., sound intensity level measured in decibels (dB)). In examples, the frequencies range from a low pitch (e.g., 250 Hz) to a high pitch (e.g., 8000 Hz), where each vertical line represents a different frequency (e.g., 250, 500, 1000, 2000, 4000, and 8000 Hz). In further examples, the intensity ranges from no sound or a soft sound (e.g., 0 dB) represented at the top of the audiogram to a loud sound (e.g., approximately 100 dB) represented at the bottom of the audiogram, where each horizontal line represents a different intensity level (e.g., 0, 20, 40, 60, 80, and 100 dB).

In some implementations, a single speaker 140 is included in or connected to the computing device 102 (or another test device) and is used to output the sounds of the test 122 to the user. Thus, the test 122 measures a hearing threshold level of both ears together and the test results 200 may include a single line 206*a* or 206*b*. In other implementations, a pair of speakers 140 (e.g., headphones, earbuds, or other right-and-left ear speaker configuration) is connected to the computing device 102 (or another test device) and is used to output the sounds of the test 122 to the user. Thus, the test 122 measures hearing thresholds of each ear independently and the test results 200 include a first line 206*a* for the right ear and a second line 206*b* for the left ear. In examples, each line 206*a* and 206*b* extends from a first threshold level for the respective ear to a second threshold level for the respective ear. A steady line 206*a* and/or 206*b* connecting the first and second thresholds (e.g., a straight line uninterrupted by peaks or valleys) indicates the user's hearing ability is consistent across the tested frequencies, which is a sign of normal hearing, where a line 206*a* and/or 206*b* with rises and drops indicates hearing loss at particular frequencies. For instance, the example test results 200 depicted in FIG. 2 indicate the user is experiencing some hearing loss for sounds around 500 Hz, 2000 Hz, and 8000 Hz in the left ear and for sounds around 250 Hz, 1000 Hz, 4000 Hz, and 8000 Hz in the right ear. In examples, a line that slopes downward for higher frequencies is common in aging-related hearing loss. In further examples, height of the line (e.g., indicating the volume level required for hearing) is a factor of interpreting the audiogram and assessing the user's hearing thresholds. For instance, a line lower on the chart indicates a higher degree of hearing loss. Other types of test results 200 are contemplated.

According to an example and with reference again to FIGS. 1A and 1B, the customized audio modification tool 120 includes a settings adjuster 124. The settings adjuster 124 receives test results 200 of the hearing test 122 and determines a customized configuration of the settings 106 based on the test results 200. In some implementations, the customized configuration increases the intensity of particular frequencies and/or reduces others to create a unique sound profile that decreases fluctuations (e.g., rises and drops) in the user's hearing levels at those particular frequencies that are indicative of hearing loss. In some implementations, the different frequencies represented in the test results (e.g., 250, 500, 1000, 2000, 4000, and 8000 Hz) correspond to the sliders or knobs (or other UI elements) representing different frequency bands of equalizer settings 106. When the customized configuration is applied to the equalizer settings 106, the sliders or knobs (or other UI elements) are moved up or down to increase or decrease the loudness (i.e., intensity) of audio output at that particular frequency band, thus providing the user a personalized and optimized listening experience. In some examples, frequency transposition techniques are additionally or alternatively implemented to shift the particular frequencies that are indicative of hearing loss to a range where they can be better perceived by the user. For instance, the customized configuration includes settings 106 that shift specific frequency bands to higher or lower frequencies using linear frequency scaling, logarithmic frequency scaling, non-linear frequency compression, and/or other processing techniques.

In some implementations, dynamic range compression is additionally or alternatively implemented to compress the range of volume levels present in audio content. For instance, the customized configuration includes settings 106 that reduce the volume of louder sounds and/or amplify softer sounds. Compressing the dynamic range of audio content can help to prevent distortion caused by audio signals that are above an intensity threshold and can also make quiet sounds (e.g., below an intensity threshold) more audible. Adjustments made to the settings 106 by applying the customized configuration causes the audio processor 110 to adjust audio output played by the application 104 to provide, what is perceived to the user to be, a "normal hearing" experience. For instance, the user experience may be characterized by lower and/or stabilized hearing threshold levels (e.g., an ability to hear softer sounds and/or a perceived consistent loudness across frequency levels).

In some implementations, an equal-loudness contour representing varying sensitivity of the human ear to different frequencies is applied to determine the customized configuration of settings 106. The equal-loudness contour is one or a combination of various equal-loudness contours (e.g., including Fletcher-Munson curves and equal loudness curves defined by the International Organization for Standardization (ISO)). For instance, applying the equal-loudness contour causes adjustments to the settings 106 that offset a known condition where humans typically do not hear all frequencies at the same volume (e.g., humans are typically most sensitive to frequencies between 2 and 5 kHz). Thus, for example, audio output at 2 kHz is perceived as louder to the user than audio output at a higher or lower frequency, even if the audio outputs are played at the same volume. In some examples, to offset a loudness fall-off at certain low and high frequencies, the equal-loudness contour is applied to boost the low and high frequencies (e.g., at lower volume levels) and produce a flatter sound profile that is perceived to be louder even at low volume. For instance, applying the equal-loudness contour prevents the perceived audio output from being dominated by mid-range frequencies (e.g., where the ear is typically most sensitive). In some implementations, the customized configuration of settings 106 includes spatial audio calibration including an adjustment to phase and/or timing of the sound signals to modify the user's spatial perception. In some examples, a personalized Head-Related Transfer Function (HRTF) is created based on the user's spatial hearing capabilities that modifies audio content to mimic the way sound waves interact with the user's head and ears to enhance the perception of direction and distance.

In other implementations, the customized configuration of settings 106 includes additional and/or alternative adjustments, such as one or a combination of: manipulation of center frequencies, control over Q-factors or bandwidths, utilization of a predefined preset, and/or other adjustments. In yet other implementations, additional information is applied to determine the customized configuration of settings 106, such as information about the speaker(s) 140 connected to the computing device 102. For instance, speaker information may include information about a sound profile of the speaker(s) 140 (e.g., based on manufacturer specifications and/or audio tests). For instance, one type of speaker 140 may have a sound profile that emphasizes bass frequencies, while another type of speaker 140 may be tuned for higher frequencies. In other examples, additional or alternative information is used to determine the customized configuration of settings 106.

Figure 3A:
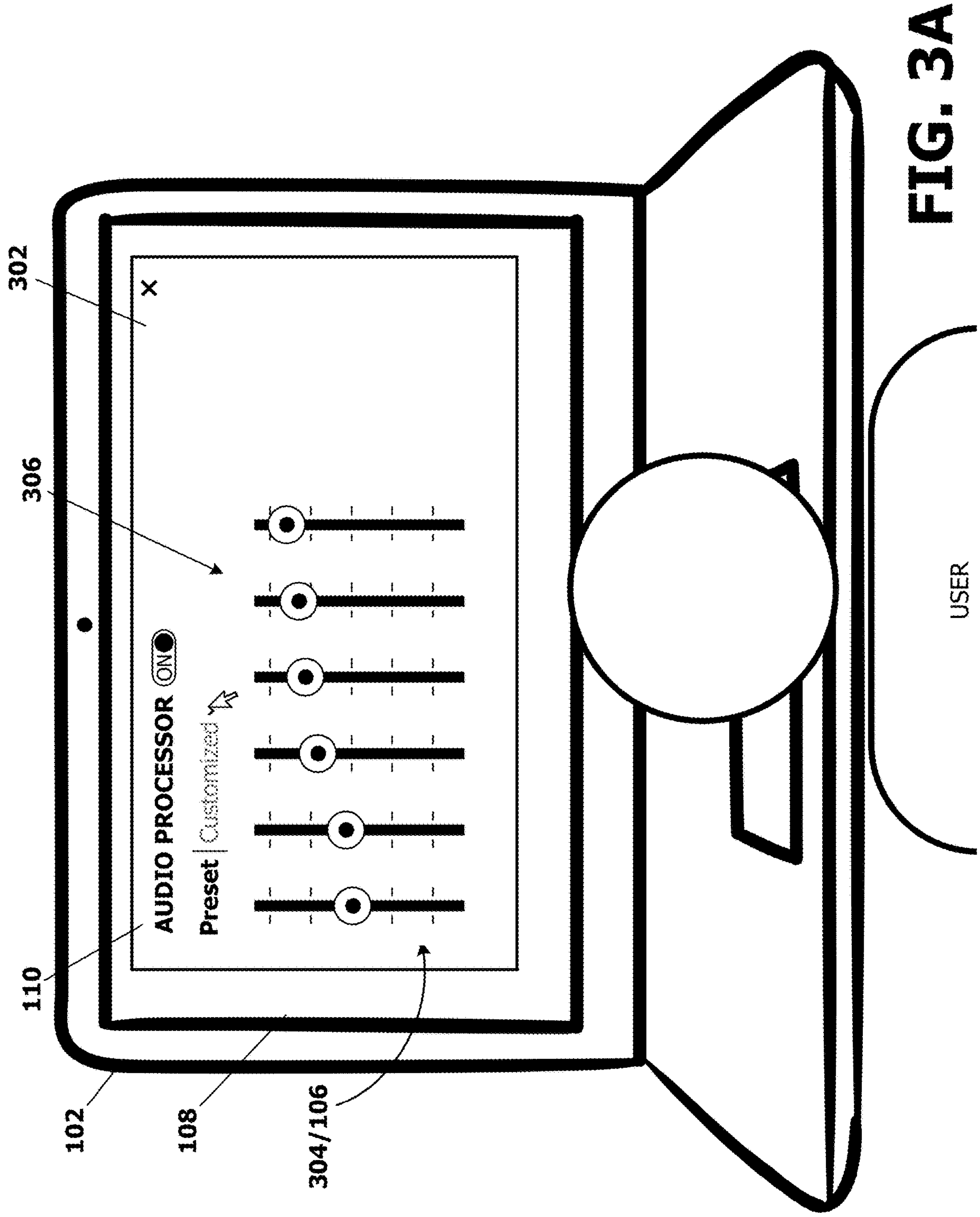
FIG. 3A depicts an example user interface for adjusting settings of an audio processor according to an aspect.

FIGS. 3A-3E depict example UIs associated with providing a customized configuration of settings 106 of an audio processor 110. With reference now to FIG. 3A, an example UI 302 is depicted on a display screen 108 of a computing device 102. The UI 302 may be opened in response to a selection of the audio processor 110 (e.g., an equalizer application or tool), a selection to adjust the settings 106, a menu selection, etc. In some examples, the audio processor 110 has a preset configuration 306 of settings 106. In further examples, the preset configuration 306 includes a configuration of frequency bands and characteristics of those frequency bands, such as the intensity level, bandwidth, center frequency, Q-factor, etc. In yet further examples, the characteristics are represented by positions of sliders 304 (or other UI elements) in relation to range of intensity levels. The sliders 304 correspond to different frequency bands and the positions correspond to different intensity levels. For instance, a first slider 304 corresponds to a first frequency band (e.g., 250 Hz), a second slider 304 corresponds to a second frequency band (e.g., 500 Hz), a third slider 304 corresponds to a third frequency band (e.g., 1000 Hz), a fourth slider 304 corresponds to a fourth frequency band (e.g., 2000 Hz), a fifth slider 304 corresponds to a fifth frequency band (e.g., 4000 Hz), and a sixth slider 304 corresponds to a sixth frequency band (e.g., 8000 Hz). In other examples, sliders 304 (or other UI elements) correspond to different frequency bands and/or other settings 106.

In some examples, the audio processor 110 provides one or more options for allowing a customized configuration of settings 106 to be selected. For instance, one or more of the sliders 304 is be moved up or down from the preset configuration 306 to a different position to create a customized configuration where the loudness (i.e., intensity) of audio output at that particular frequency band is increased or decreased accordingly. In some examples, other characteristics of audio are also manually adjusted.

Figure 3B:
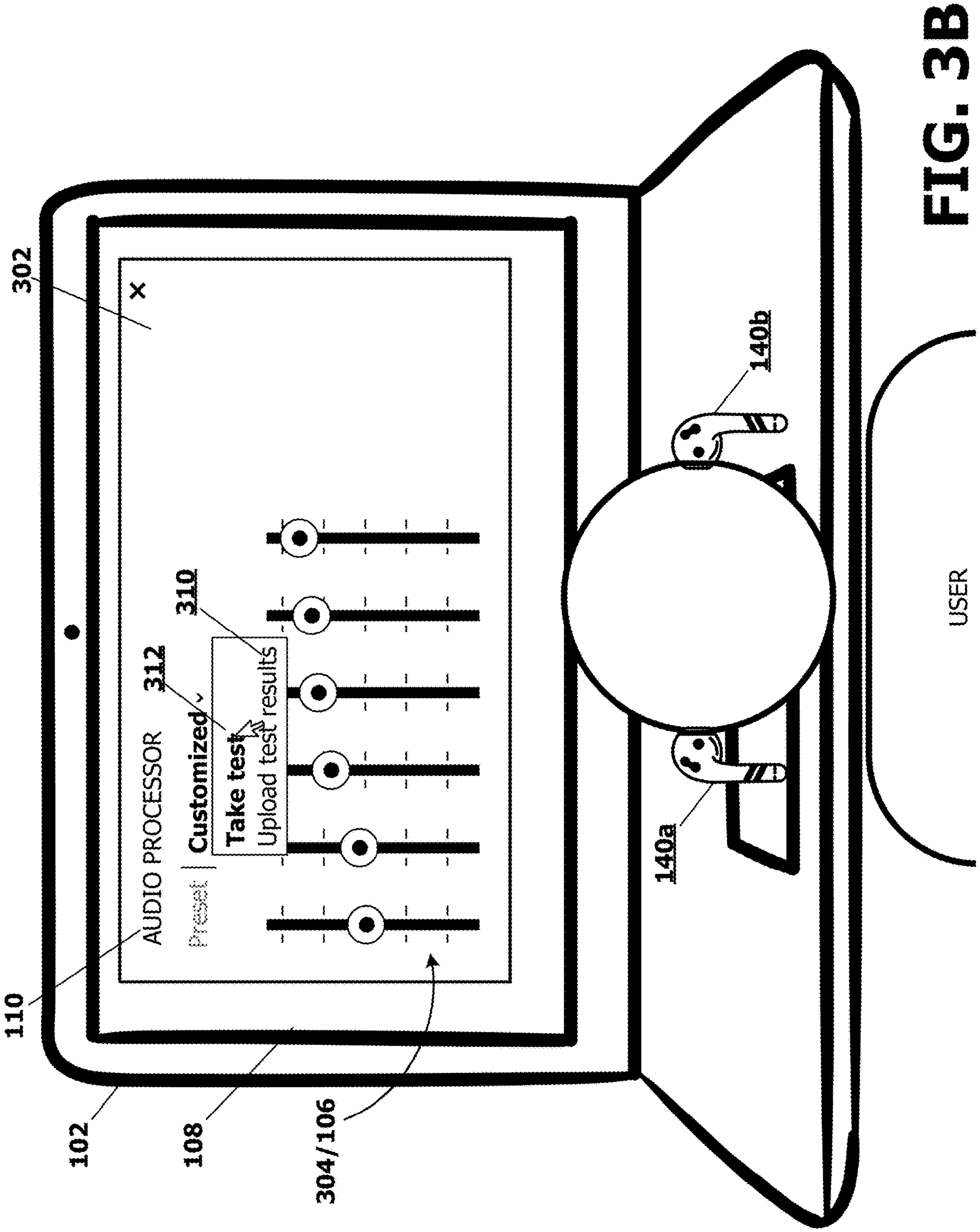
FIG. 3B depicts an example option for determining a customized configuration of settings based on results of a hearing test according to an aspect.

In some implementations, and as depicted in FIG. 3B, the audio processor 110 provides one or more options 310 and 312 to select a customized configuration of settings 106 based on results of a hearing test 122. A selection for a customized configuration of settings 106 based on hearing test results causes the customized audio modification tool 120 to initiate a process for determining and applying the customized configuration to the settings 106. In some examples, a first option 310 is provided to upload results of a previous test 122 (e.g., results from an audiometry test performed by a healthcare provider or as part of installing an audio device). In other examples, a second option 312 is provided, which, when selected, initiates a hearing test 122 provided by the customized audio modification tool 120.

Figure 3C:
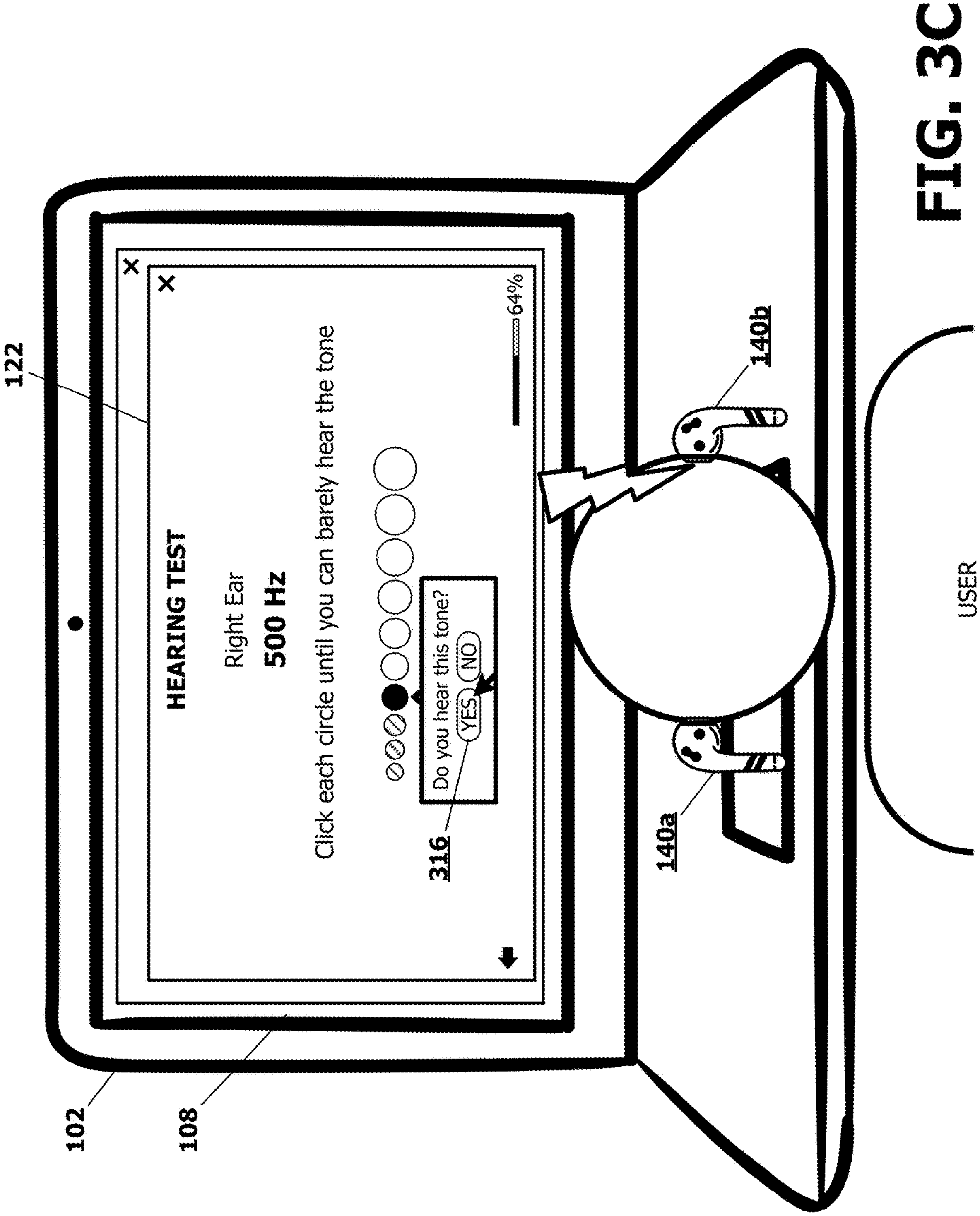
FIG. 3C depicts an example hearing test according to an aspect.

An example hearing test 122 is depicted in FIG. 3C. In the example hearing test 122, the user is led through a series of evaluations, where, in each evaluation, a test sound (e.g., audio output) is played at a particular frequency and intensity level via a particular speaker 140*a* or 140*b*. The intensity level of the test sound is increased from a low intensity level to a higher intensity level until it is detected by the user as indicated by a received user response 314. The evaluations are performed across a range of frequencies and, in some examples, for each ear. Accordingly, test results are determined based on the received user responses 314. As should be appreciated, the depicted example is one example of various types of hearing tests 122 that may be provided by the customized audio modification tool 120.

Figure 3D:
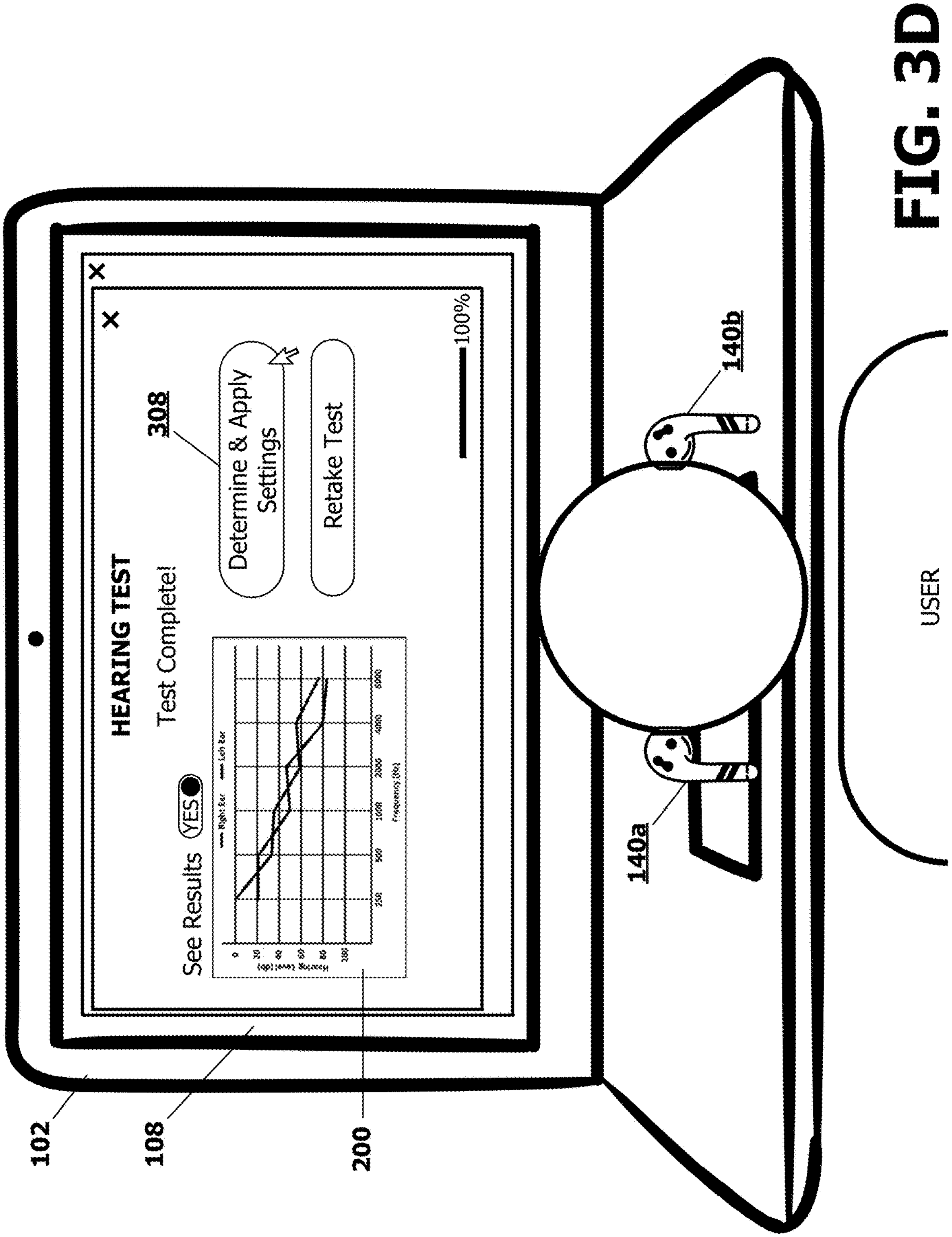
FIG. 3D depicts example hearing test results and an example option to generate a customized configuration of settings based on the hearing test results according to an aspect.

Example results of the hearing test 122 are depicted in FIG. 3D, where the test results 200 represent the user's hearing threshold levels (e.g., the user's ability to hear the test sounds) at various frequencies. In some examples, the test results 200 are automatically used to determine a customized configuration to the settings 106 that compensates for drops in hearing threshold levels indicative of hearing loss. In other examples, an option 308 is provided to selectively use the test results 200 to determine the customized configuration to the settings 106. In some examples, at least a portion of the drops in hearing threshold levels is related to hearing loss of the user (e.g., sensorineural hearing loss, conductive hearing loss, or mixed hearing loss). In further examples, at least a portion of the drops in hearing threshold levels is related to characteristics of the speaker(s) 140. For instance, the quality and characteristics of the speakers 140 used to deliver the test sounds and other audio content can impact how the test sounds and other audio content is perceived by the user. In further examples, at least a portion of the drops in hearing threshold levels is related to the listening environment. For instance, the presence of background noise and/or audio reflection/absorption characteristics of the environment may mask test sounds and other audio content (e.g., in particular at lower intensity levels).

Figure 3E:
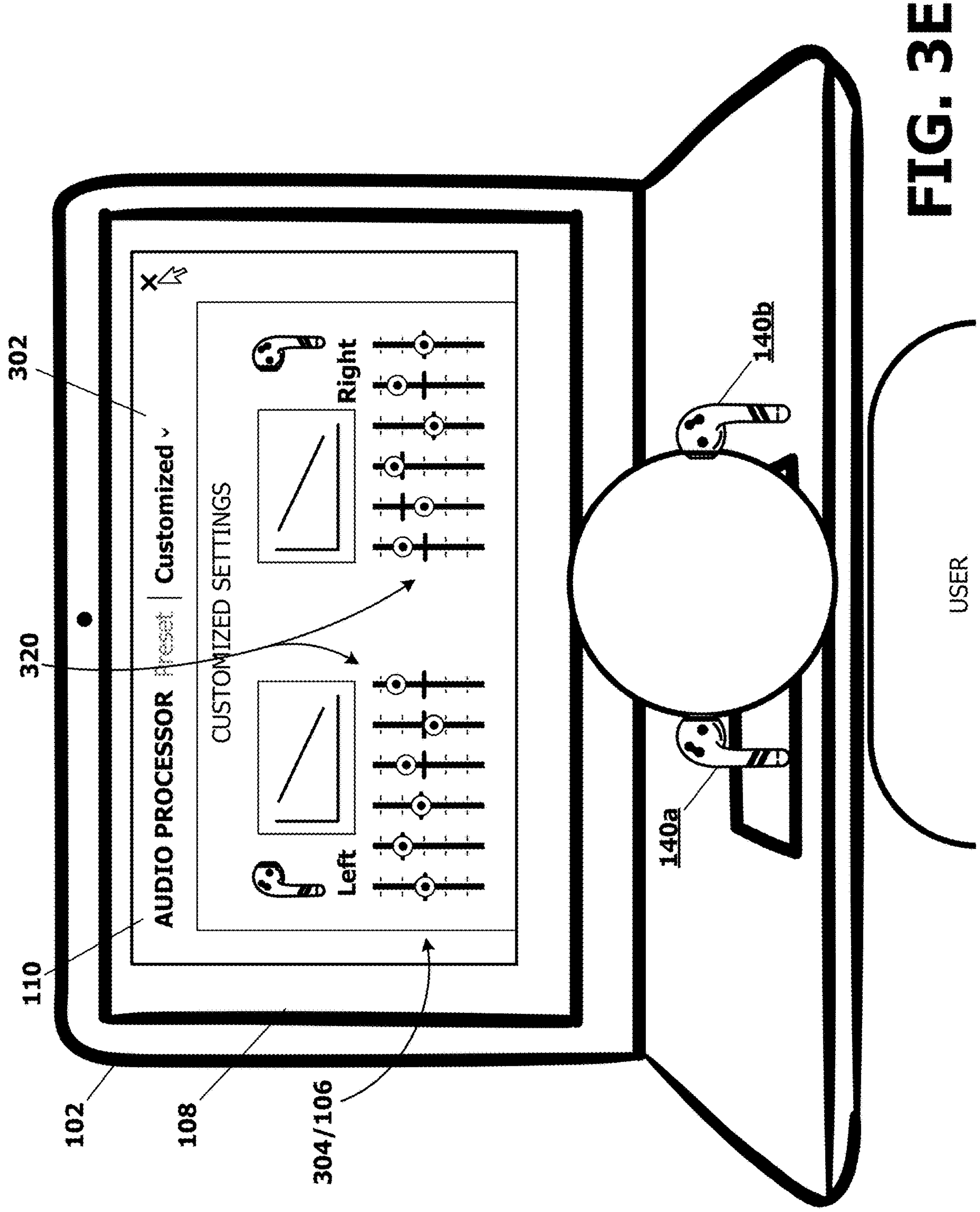
FIG. 3E depicts an example customized configuration of settings determined based on the hearing test results according to an aspect.

An example customized configuration 320 of settings 106 is depicted in FIG. 3E. In some examples, the customized configuration 320 includes settings 106 for a plurality of audio channels (e.g., a right channel for the right ear and a left channel for the left ear) determined based on the test results 200. In other examples, values corresponding to the user's hearing threshold levels are averaged out for both ears, where the same settings 106 are applied to both the right and left channels. In some examples, the customized configuration 320 compensates for drops in hearing threshold levels in the test results 200 and causes the audio processor 110 to adjust the audio output to have a sound profile that is perceived by the user as having a similar intensity level (e.g., consistently loud) across frequency bands. In other examples, the customized configuration 320 compensates for drops in hearing threshold levels in the test results 200 by shifting the particular frequencies corresponding to the drops in hearing threshold levels to a range (e.g., higher or lower frequency bands) where they can be better perceived by the user. In other examples, the customized configuration 320 reduces the volume of louder sounds and/or amplifies softer sounds to help prevent a perceived distortion. In some implementations, one or more options are provided that allow the user to select whether to apply the customized configuration 320 of settings 106 to one application 104 or across multiple applications 104. In other implementations, additional and/or alternative options are provided.

Figure 4:
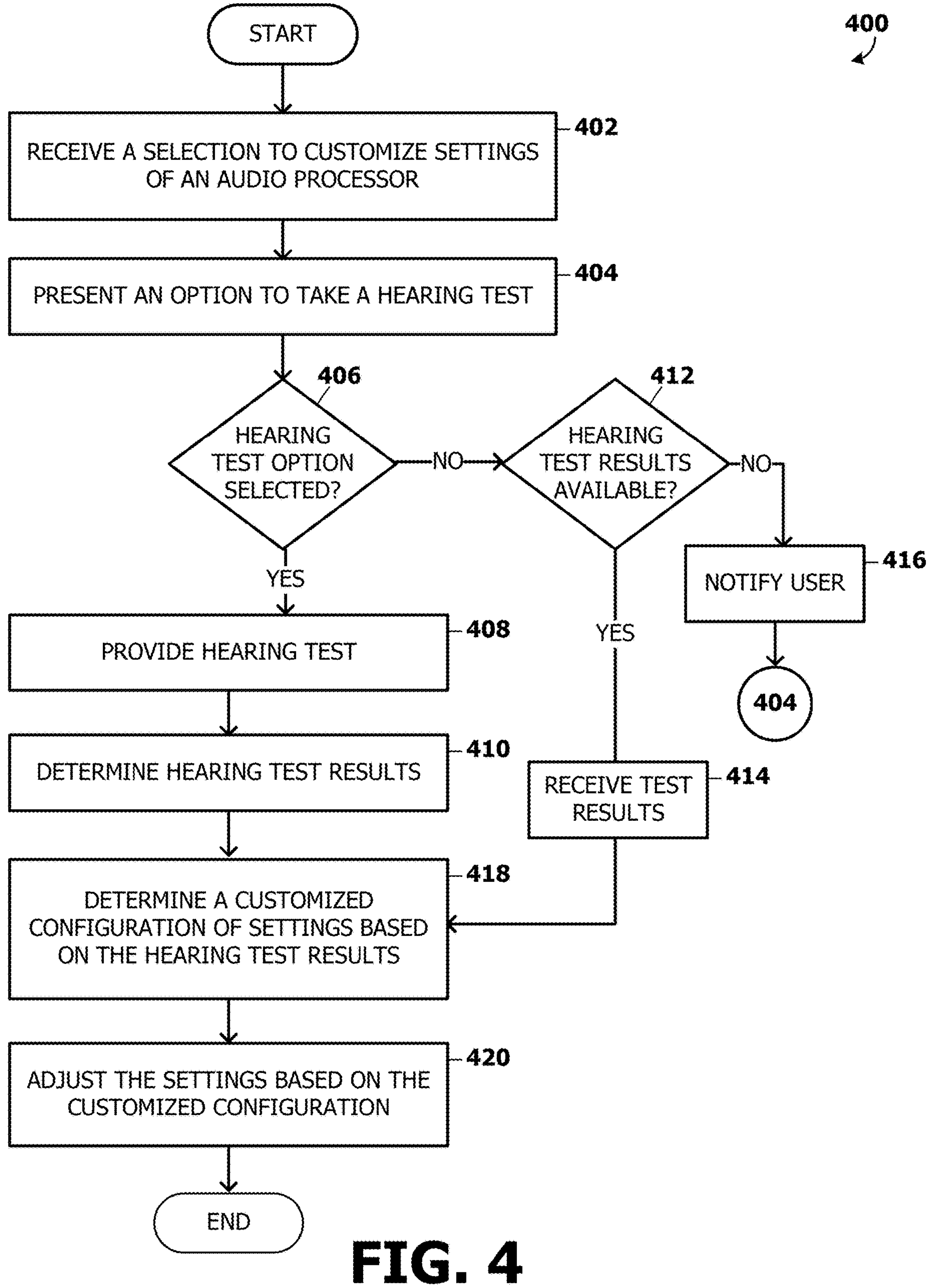
FIG. 4 is a flow diagram depicting an example method of generating and applying a customized configuration of settings to an audio processor according to an aspect.

With reference now to FIG. 4, a flow diagram is depicted of an example method 400 of generating and applying a customized configuration 320 of settings 106 to an audio processor 110 according to an aspect. At operation 402, an indication of a selection to customize settings 106 is received. In some implementations, a prompt is provided that informs the user that the audio processor 110 can be configured with settings 106 that are customized to the user based on the user's hearing abilities/losses. For instance, the prompt may include a link to access the customized audio modification tool 120 to generate the customized configuration 320 of settings 106. In other examples, one or more options 310 and 312 are provided by an application 104 and/or the audio processor 110 for allowing the user to select to apply a customized configuration of settings 106 to the audio processor 110. In yet other examples, the indication of the selection to customize settings 106 corresponds to a user command, selection of an option in a menu or settings application, or another selection method.

In some implementations, an option to take a hearing test 122 is presented at operation 404 and a determination is made at decision operation 406 as to whether the option is selected. When the option to take the hearing test 122 is selected, the method 400 proceeds to operation 408, where the hearing test 122 is provided to the user. In some implementations, the hearing test 122 includes leading the user through a series of evaluations, where, in each evaluation, a test sound (e.g., audio output) is played by a particular speaker 140 at a particular frequency and intensity level, which is incrementally increased until it is detected by the user. For instance, the user may provide a user response 314 when the test sound is heard. The evaluations are performed across a range of frequencies and, in some examples, for each ear. In other implementations, another type of hearing test 122, such as a spatial audio test, is provided to the user.

At operation 410, test results 200 are determined based on the received user responses 314. The test results 200 represent the user's hearing threshold levels at various frequency bands. In examples, low hearing threshold levels (e.g., drops or inconsistencies in a frequency-intensity line representing the user's hearing ability across different frequencies) indicate a corresponding level of hearing loss experienced by the user at those particular frequencies.

In some implementations, if a determination is made that the option to take the hearing test 122 is not selected at decision operation 406, a determination is made at decision operation 412 as to whether test results 200 of a previously taken hearing test 122 are available. The previously taken hearing test 122 may have been provided by the customized audio modification tool 120 or by another entity. In some examples, an indication of a selection to upload test results 200 of a previously taken hearing test 122 is received at decision operation 412, and the method 400 proceeds to operation 414 where the test results 200 of the previously taken hearing test 122 are received. In other examples, an indication to upload test results 200 of a previously taken hearing test 122 is not received at decision operation 412. In such examples, a notification may be provided to inform the user that a hearing test 122 is a prerequisite to automatically customize equalizer settings 106 based on the user's hearing abilities/loss. The method 400 may then return to operation 404 where the option to take the hearing test 122 is once again provided to the user.

In other examples, when the hearing test results 200 are determined (at operation 410) or received (at operation 414), the method 400 proceeds to operation 418 where a customized configuration 320 of settings 106 is determined based on the test results 200. In some examples, the intensity levels of different frequency bands may be increased (or decreased) in the customized configuration 320 to compensate for drops in the user's hearing threshold levels corresponding to hearing loss determined based on the test results 200. In further examples, the intensity levels of different frequency bands may be increased (or decreased) in different channels of audio output (e.g., a right channel for a first speaker 140*a* for the right ear and a left channel for a second speaker 140*b* for the left ear). In yet further examples, the customized configuration causes audio signals at particular frequencies corresponding to the drops in hearing threshold levels to be shifted to a higher or lower frequency band range where the user is able to better perceive the audio. In other examples, the customized configuration 320 reduces the volume of louder sounds and/or amplifies softer sounds to help prevent distortion. In other examples, the customized configuration 320 adjusts phase and/or timing of the sound signals to modify the user's spatial perception. In yet other examples, a personalized HRTF is created to modify direction and/or distance perception. In further examples, an equal-loudness contour representing varying sensitivity of the human ear to different frequencies is applied to determine the customized configuration of settings 106. One or more types of adjustments (e.g., frequency transposition techniques) may not be applied to one or more types of audio content (e.g., copyrighted material, audio with Digital Rights Management (DRM) protection, licensed content). At operation 420, the customized configuration 320 is applied to the settings 106. For instance, one or more settings 106 are adjusted based on the determined customized configuration 320. Accordingly, when the audio processor 110 is used, the audio processor 110 adjusts the audio content data according to the customized configuration 320 of settings 106. When the adjusted audio content data is played by the speaker(s) 140, the audio output is adjusted to compensate for drops in the user's hearing threshold levels and the user is provided with an improved listening experience.

Figure 5:
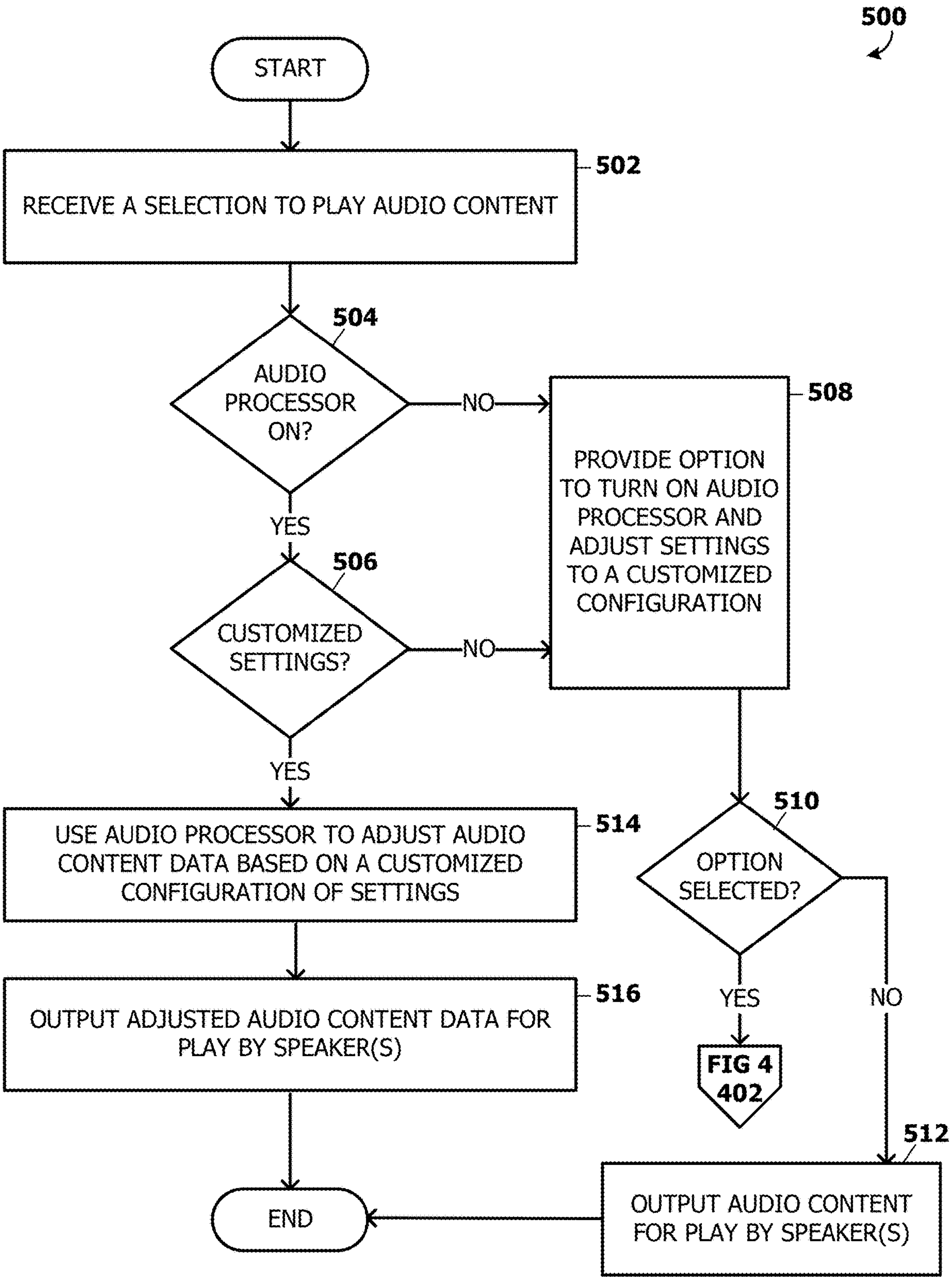
FIG. 5 is a flow diagram depicting an example method of playing audio content adjusted by an audio processor based on a customized configuration of settings according to an aspect.

With reference now to FIG. 5, a flow diagram is depicted of an example method 500 of generating and applying a customized configuration 320 of settings 106 to an audio processor 110 according to an aspect. For instance, the operations included in the example method 500 may be performed by an application 104 that includes functionality to read and play audio content (e.g., an audio file or other audio signals). In examples, the application 104 further includes or is in communication with an audio processor 110 that adjusts audio played by the application based on a preset configuration 306 or a customized configuration 320 of settings 106. At operation 502, an indication of a selection to play audio content is received. The audio content may be in one of various types of audio that the application 104 is configured to read and play.

In some implementations, at decision operation 504, a determination is made as to whether the audio processor 110 is turned on. For instance, an option may be provided to turn the audio processor 110 on or off. In other implementations, the audio processor 110 is in an "always on" state. When the audio processor 110 is on, the method 500 proceeds to decision operation 506 where a determination is made as to whether the settings 106 are part of a preset configuration 306 or a customized configuration 320.

In some implementations, when the settings 106 are part of a preset configuration 306, an option is presented at operation 508 notifying the user that the settings 106 can be custom configured based on the user's hearing abilities/loss. When a determination is made at decision operation 510 that the option to customize the settings 106 is selected, the method 500 continues to operation 402 of method 400 where a customized configuration 320 of settings 106 is determined and applied to the audio processor 110 according to an aspect. When a determination is made at decision operation 510 that the option to customize the settings 106 is not selected, the audio content is played either non-adjusted or adjusted based on the preset configuration 306 of settings 106 at operation 512.

In other implementations, at decision operation 506, the settings 106 are determined to be part of a customized configuration 320 determined by the customized audio modification tool 120 and the method 500 proceeds to operation 514 where the audio processor 110 adjusts the audio content data based on the customized configuration 320 of settings 106. For instance, the audio processor 110 uses the settings 106 to adjust one or more characteristics of one or more frequency bands of one or more audio channels.

At operation 516, the adjusted audio content data is provided to a sound card (or interface) for output by one or more connected speakers 140. When the adjusted audio content data is played by the speaker(s) 140, the audio output is adjusted to compensate for drops in the user's hearing threshold levels (e.g., determined based on results 200 of a hearing test 122) and/or other factors and the user is provided with an improved listening experience. In some examples, the frequency balance of the audio output, as perceived by the user, matches a desired experience, such as the experience of a person in an ideal environment experiencing the audio as captured by a microphone.

FIG. 6 and the associated description provide a discussion of a variety of operating environments in which examples of the invention may be practiced. However, the devices and systems illustrated and discussed with respect to FIG. 6 is for purposes of example and illustration and is not limiting of a vast number of computing device configurations that may be utilized for practicing aspects of the invention, described herein. FIG. 6 is a block diagram illustrating physical components (i.e., hardware) of a computing device 600 with which examples of the present disclosure may be practiced. In a basic configuration, the computing device 600 may include at least one processing unit and a system memory 604. in examples, the processing unit(s) (e.g., processors) are referred to as a processing system 602. Depending on the configuration and type of computing device, the system memory 604 may comprise volatile storage (e.g., random access memory), non-volatile storage (e.g., read-only memory), flash memory, or any combination of such memories. The system memory 604 may include an operating system 605 and one or more program modules 606 suitable for running software applications 650 (e.g., the audio processor 110, customized audio modification tool 120, and/or an application 104 including or in communication with the audio processor 110 and the customized audio modification tool 120).

The operating system 605, for example, may be suitable for controlling the operation of the computing device 600. Furthermore, aspects of the invention may be practiced in conjunction with a graphics library, other operating systems, or any other application program and is not limited to any particular application or system. This basic configuration is illustrated in FIG. 6 by those components within a dashed line 608. The computing device 600 may have additional features or functionality. For example, the computing device 600 may also include additional data storage devices (removable and/or non-removable) such as, for example, magnetic disks, optical disks, or tape. Such additional storage is illustrated in FIG. 6 by a removable storage device 609 and a non-removable storage device 610.

As stated above, a number of program modules and data files may be stored in the system memory 604. While executing on the processing system 602, the program modules 606 may perform processes including one or more of the operations of the methods illustrated in FIG. 4 and/or FIG. 5. Other program modules that may be used in accordance with examples of the present invention and may include applications such as electronic mail and contacts applications, word processing applications, spreadsheet applications, database applications, slide presentation applications, drawing or computer-aided application programs, etc.

Furthermore, examples of the invention may be practiced in an electrical circuit comprising discrete electronic elements, packaged or integrated electronic chips containing logic gates, a circuit utilizing a microprocessor, or on a single chip containing electronic elements or microprocessors. For example, examples of the invention may be practiced via a system-on-a-chip (SOC) where each or many of the components illustrated in FIG. 6 may be integrated onto a single integrated circuit. Such an SOC device may include one or more processing units, graphics units, communications units, system virtualization units and various application functionality all of which are integrated (or "burned") onto the chip substrate as a single integrated circuit. When operating via an SOC, the functionality, described herein, with respect to generating suggested queries, may be operated via application-specific logic integrated with other components of the computing device 600 on the single integrated circuit (chip). Examples of the present disclosure may also be practiced using other technologies capable of performing logical operations such as, for example, AND, OR, and NOT, including mechanical, optical, fluidic, and quantum technologies.

The computing device 600 may also have one or more input device(s) 612 such as a keyboard, a mouse, a pen, a sound input device, a touch input device, etc. The output device(s) 614 such as a display, speakers, a printer, etc. may also be included. The aforementioned devices are examples and others may be used. The computing device 600 may include one or more communication connections 616 allowing communications with other computing devices 618. Examples of suitable communication connections 616 include RF transmitter, receiver, and/or transceiver circuitry; universal serial bus (USB), parallel, and/or serial ports.

The term computer readable media as used herein may include computer storage media. Computer storage media may include volatile and nonvolatile, removable and non-removable media implemented in any method or technology for storage of information, such as computer readable instructions, data structures, or program modules. The system memory 604, the removable storage device 609, and the non-removable storage device 610 are all computer storage media examples (i.e., memory storage.) Computer storage media may include RAM, ROM, electrically erasable programmable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing device 600. Any such computer storage media may be part of the computing device 600. Computer storage media does not include a carrier wave or other propagated data signal.

Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, communication media may include wired media such as a wired network or direct-wired connection, and wireless media such as acoustic, radio frequency (RF), infrared, and other wireless media.

According to an aspect, a method is provided, comprising: determining a customized configuration of settings for an audio processor based on results of a hearing test, where the results indicate hearing loss experienced by a user; adjusting the audio processor settings based on the customized configuration; receiving an audio content; adjusting playback of the audio content based on the customized configuration of audio processor settings; and providing the adjusted audio content to a sound interface for output by a speaker.

According to another aspect, a system is provided, comprising: a processing system; and memory storing instructions that, when executed, cause the system to perform operations comprising: receiving an indication of a selection to customize settings of an audio processor; providing a hearing test to a user; receiving user responses in association with the hearing test; determining results of the hearing test based on the user responses, wherein the results indicate hearing loss experienced by the user; determining a customized configuration of the settings based on the results; and adjusting the settings based on the customized configuration.

According to another aspect, a device is provided, comprising: an audio processor; a processing system; and memory storing instructions that, when executed, cause the device to perform operations comprising: receiving an indication of a selection to customize settings of the audio processor; receiving results of a hearing test, wherein the results indicate a hearing threshold level experienced by at least one ear of the user; determining a customized configuration of the settings based on the results; adjusting the settings based on the customized configuration; receiving audio content; providing the audio content to the audio processor to adjust output of the audio content based on the customized configuration of settings; receiving, from the audio processor, adjusted audio content; and providing the adjusted audio content to a sound interface for output by a speaker.

Aspects of the present invention, for example, are described above with reference to block diagrams and/or operational illustrations of methods, systems, and computer program products according to aspects of the invention. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved. Further, as used herein and in the claims, the phrase "at least one of element A, element B, or element C" is intended to convey any of: element A, element B, element C, elements A and B, elements A and C, elements B and C, and elements A, B, and C.

The description and illustration of one or more examples provided in this application are not intended to limit or restrict the scope of the invention as claimed in any way. The aspects, examples, and details provided in this application are considered sufficient to convey possession and enable others to make and use the best mode of claimed invention. The claimed invention should not be construed as being limited to any aspect, example, or detail provided in this application. Regardless of whether shown and described in combination or separately, the various features (both structural and methodological) are intended to be selectively included or omitted to produce an example with a particular set of features. Having been provided with the description and illustration of the present application, one skilled in the art may envision variations, modifications, and alternate examples falling within the spirit of the broader aspects of the general inventive concept embodied in this application that do not depart from the broader scope of the claimed invention.

I claim:

1. A method, comprising:

determining a customized configuration of audio processor settings for an audio processor based on results of a hearing test that indicate hearing loss experienced by a user at a first frequency band, wherein determining the customized configuration comprises:

applying an equal-loudness contour to the audio processor settings;

based on the equal-loudness contour, determining an adjusted level of intensity of the first frequency band that offsets a perceived loudness fall-off at the frequency band; and setting an intensity level of the first frequency band to the adjusted level of intensity;

adjusting the audio processor settings based on the customized configuration;

receiving an audio content;

adjusting playback of the audio content based on the customized configuration of audio processor settings; and providing the adjusted audio content to a sound interface for output by a speaker.

2. The method of claim 1, wherein prior to receiving the results of the hearing test:

providing the hearing test;

receiving user responses in association with the hearing test; and determining the results based on the user responses.

3. The method of claim 2, wherein the results represent a hearing threshold level of each or a combination of the user's ears for audio output across various frequency bands and at different intensity levels.

4. The method of claim 1, wherein:

the results indicate additional hearing loss experienced by the user at a second frequency band;

determining the customized configuration comprises determining a second adjusted level of intensity of the second frequency band that compensates for the additional hearing loss experienced by the user; and adjusting the audio processor settings comprises setting the intensity level of the second frequency band to the second adjusted level of intensity.

5. The method of claim 1, wherein:

determining the customized configuration further comprises determining:

a maximum intensity threshold of each of a plurality of frequency bands; and a minimum intensity threshold of each of the plurality of frequency bands; and adjusting the audio processor settings comprises, for each of the plurality of frequency bands, compressing an amplitude based on the maximum intensity threshold and the minimum intensity threshold of the frequency band.

6. The method of claim 1, wherein:

determining the customized configuration further comprises determining a second frequency band at which the results indicate hearing loss experienced by the user is less than at the first frequency band; and adjusting the audio processor settings comprises shifting the first frequency band to the second frequency band.

7. The method of claim 1, further comprising:

providing an option for uploading the results of the hearing test; and in response to a selection of the option, receiving the results.

8. A system, comprising:

a processing system; and memory storing instructions that, when executed, cause the system to perform operations comprising:

receiving an indication of a selection to customize settings of an audio processor;

providing a hearing test to a user;

receiving user responses in association with the hearing test;

determining results of the hearing test based on the user responses, wherein the results indicate hearing loss experienced by the user at a first frequency band;

determining a customized configuration of the settings based on the results by:

applying an equal-loudness contour to the settings of the audio processor;

based on the equal-loudness contour, determining an adjusted level of intensity of the first frequency band that offsets a perceived loudness fall-off at the first frequency band; and setting an intensity level of the first frequency band to the adjusted level of intensity; and adjusting the settings based on the customized configuration.

9. The system of claim 8, wherein the operations further comprise:

receiving, by the audio processor, audio content;

adjusting, by the audio processor, playback of the audio content based on the customized configuration of the settings; and providing, by the audio processor to a sound interface, adjusted audio content for output by a speaker.

10. The system of claim 8, wherein:

the results represent a hearing threshold level of each or a combination of the user's ears for audio output across various frequency bands and at different intensity levels; and the results indicate a low hearing threshold level experienced by the user at the first frequency band.

11. The system of claim 10, wherein:

the first adjusted level of intensity compensates for the low hearing threshold level experienced by the user.

12. The system of claim 10, wherein:

the customized configuration comprises a second frequency band at which the results indicate hearing loss experienced by the user is less than at the first frequency band; and adjusting the settings comprises shifting the first frequency band to the second frequency band.

13. The system of claim 8, wherein:

the customized configuration comprises at least one of:

a maximum intensity threshold of the first frequency band; or a minimum intensity threshold of the first frequency band; and adjusting the settings comprises compressing a dynamic range of intensity of the first frequency band via setting at least one of:

a first compression level of the intensity of the first frequency band to the maximum intensity threshold; or a second compression level of the intensity of the first frequency band to the minimum intensity threshold.

14. A device, comprising:

an audio processor;

a processing system; and memory storing instructions that, when executed, cause the device to perform operations comprising:

receiving an indication of a selection to customize settings of the audio processor;

receiving results of a hearing test, wherein the results indicate a hearing threshold level experienced by at least one ear of the user at a first frequency band;

determining a customized configuration of the settings based on the results by:

applying an equal-loudness contour to the settings of the audio processor;

based on the equal-loudness contour, determining an adjusted level of intensity of the first frequency band that offsets a perceived loudness fall-off at the first frequency band; and setting an intensity level of the first frequency band to the adjusted level of intensity;

adjusting the settings based on the customized configuration;

receiving audio content;

providing the audio content to the audio processor to adjust output of the audio content based on the customized configuration of settings;

receiving, from the audio processor, adjusted audio content; and providing the adjusted audio content to a sound interface for output by a speaker.

15. The device of claim 14, further comprising, prior to receiving the results of the hearing test:

providing the hearing test;

receiving user responses in association with the hearing test; and determining the results based on the user responses.

16. The device of claim 14, wherein determining the customized configuration comprises performing at least one of:

equalization;

frequency range transposition;

dynamic range compression; or audio multiband compression.

17. The device of claim 14, wherein the results represent a hearing threshold level of each or a combination of the user's ears for audio output across various frequency bands and at different intensity levels.

18. The device of claim 14, wherein:

determining the customized configuration comprises determining:

a maximum intensity threshold of each of a plurality of frequency bands; and a minimum intensity threshold of each of the plurality of frequency bands; and adjusting the audio processor settings comprises, for each of the plurality of frequency bands, compressing an amplitude based on the maximum intensity threshold and the minimum intensity threshold of the frequency band.

19. The device of claim 14, wherein:

determining the customized configuration further comprises determining a second frequency band at which the results indicate hearing loss experienced by the user is less than at the first frequency band; and adjusting the audio processor settings comprises shifting the first frequency band to the second frequency band.

20. The device of claim 14, the operations further comprising:

prior to receiving the results of the hearing test, providing an option for uploading the results; and in response to a selection of the option, receiving the results.

* * * * *